US00PP16240P3

(12) United States Plant Patent
Edmonds et al.

(10) Patent No.: US PP16,240 P3
(45) Date of Patent: Feb. 7, 2006

(54) ***LONICERA PERICLYMENUM* PLANT NAMED 'SCENTSATION'**

(50) Latin Name: *Lonicera periclymenum*
Varietal Denomination: Scentsation

(75) Inventors: John Edmonds, Hereford (GB); Elisabeth Wilms, Hereford (GB)

(73) Assignee: J. Tooby and Co. Ltd., Bransford (GB)

( * ) Notice: Subject to any disclaimer, the term of this patent is extended or adjusted under 35 U.S.C. 154(b) by 0 days.

(21) Appl. No.: 10/425,898

(22) Filed: Apr. 28, 2003

(65) Prior Publication Data

US 2003/0204887 P1 Oct. 30, 2003

(30) Foreign Application Priority Data

Apr. 29, 2002 (QZ) ..... PBR 2002/0559

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent Bell
(74) *Attorney, Agent, or Firm*—Christie, Parker & Hale, LLP

(57) ABSTRACT

A new plant variety of *Lonicera periclymenum* characterized by its fragrant and abundant flowers.

1 Drawing Sheet

Figure 1:
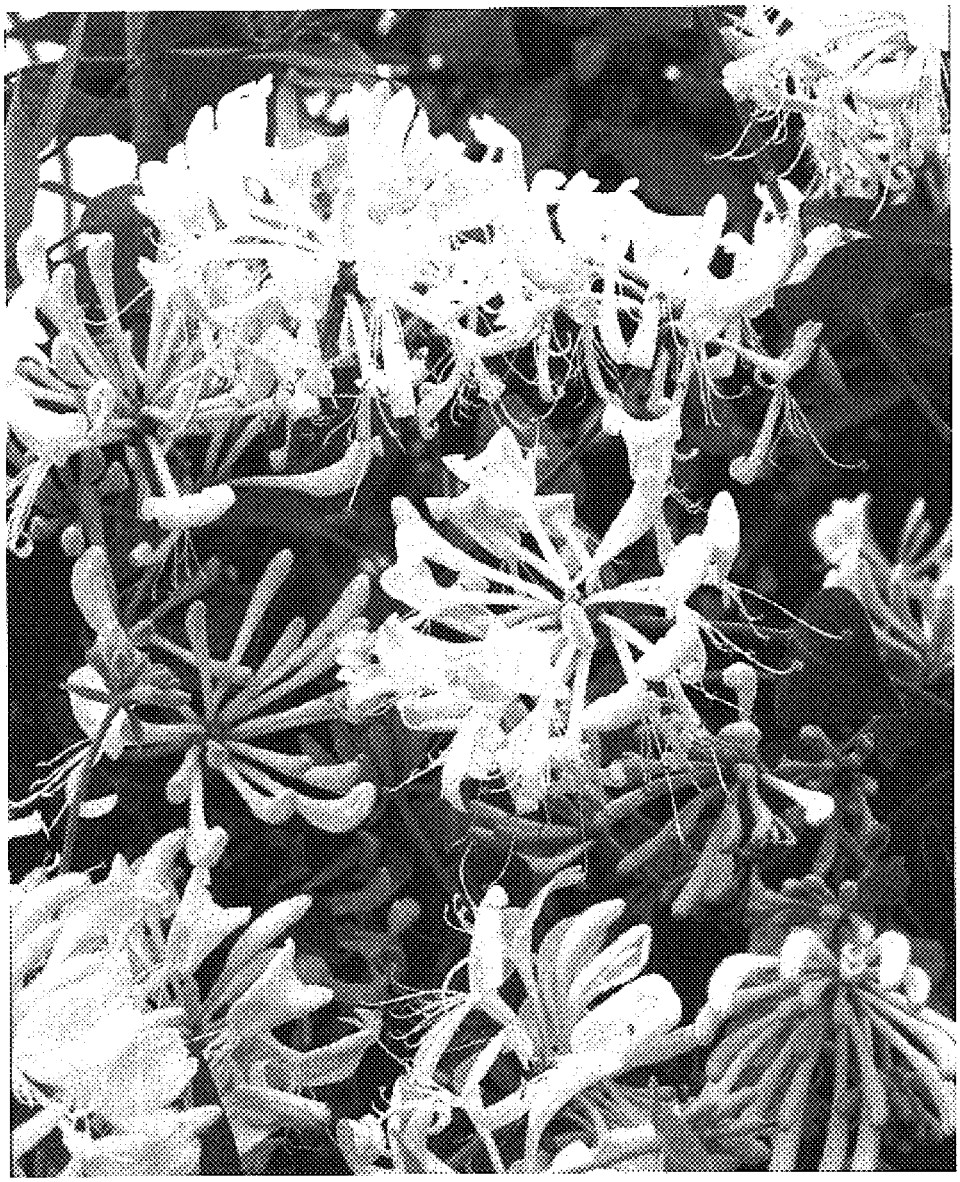

Botanical classification: *Lonicera periclymenum,* c.v. 'Scentsation'.

BACKGROUND OF THE INVENTION

The present invention relates to a new and distinct variety of *Lonicera periclymenum* L., which was discovered as a naturally occurring branch sport of an unnamed, unpatented variety of *Lonicera periclymenum* plant by John Edmunds and Elisabeth Wilms in Herefordshire, Great Britain. The varietal denomination of the new variety is 'Scentsation'.

The genus *Lonicera* is included in the family Caprifoliaceae which comprises about 15 genera of shrubs growing in the northern and southern hemispheres. *Lonicera* comprises over 200 species of deciduous or evergreen shrubs, and erect or climbing shrubs, many of which possess desirable ornamental characteristics.

*Lonicera periclymenum* is a twining shrub native to Europe, North Africa and western Asia, with ovate to ovate-oblong leaves the undersides of which are colored bluish green. Flowers of *L. periclymenum* appear in whorls in summer and are two-lipped and pale yellow in color.

SUMMARY OF THE INVENTION

The new variety was discovered as a branch sport of an unnamed, unpatented variety of *Lonicera periclymenum* and differs from its parent in having more fragrant and more abundant flowers. Asexual reproduction of the new variety by stem cuttings, performed in Herefordshire, Great Britain and Vacaville, Calif. have confirmed that the distinctive characteristics of the new variety are stable and transmitted to succeeding generations, and the new variety reproduces true to type.

COMPARISON WITH PARENT

'Scentsation' is distinguished from its parent and all other varieties of *Lonicera periclymenum* of which I am aware, including the most similar variety, *Lonicera periclymenum* 'Graham Thomas' (not patented) in having more fragrant and more abundant flowers.

BRIEF DESCRIPTION OF ILLUSTRATION

The accompanying photographic illustration shows a specimen of the new cultivar as true to color as is reasonably possible to make in an illustration of this character. The photographic illustration is of a one-year old plant grown outdoors in 1-gallon containers in Vacaville, Calif.

FIG. 1 illustrates the typical flowers of 'Scentsation'.

DETAILED DESCRIPTION OF THE NEW VARIETY

'Scentsation' has not been observed under all possible environmental, cultural and light conditions. The following observations and descriptions are of one-year-old plants grown outdoors in 1-gallon containers in Vacaville, Calif. In this description, color references are to The Royal Horticultural Society Colour Chart (1995) and terminology used in the color descriptions herein refers to plate numbers in this color chart. Phenotypic expression may vary with light intensity, cultural and environmental conditions.

Classification:

*Botanical.*—*Lonicera periclymenum* L. 'Scentsation'.

*Parentage.*—Branch sport of unnamed, unpatented variety of *Lonicera periclymenum.*

*Propagation.*—By vegetative cuttings.

Plant:

*Size.*—Mature plant can climb and spread to about 10 meters at maturity.

*Habit.*—A scrambling, twining vine that can be grown on the ground, or allowed to climb screens or trellises.

*Branching.*—Opposite, sparse.

*Leaf description.*—Arrangement: Simple, opposite on stems. Leaf shape: Ovate to sublanceolate. Apex: Acute to obtuse. Base: Cuneate. Leaf size: Juvenile:

2 to 4 cm long and 1.5 to 2 cm wide. Mature: 5 to 7.5 cm long and 1.5 to 2.8 cm wide. Leaf margin: Entire. Leaf texture and substance: Adaxial: Smooth, glossy; slightly impressed veins. Abaxial: Pubescent. Immature leaf color: Adaxial: Near Green Group 137B. Abaxial: Near Green Group 138B. Midrib: Near Yellow-Green Group 145B. Mature leaf color: Adaxial: Near Green Group 137C. Abaxial: Near Greyed-Green Group 191B. Stem color: Juvenile Stem: Near Green Group 143A; Mature Stem: Near Greyed-Green Group 197A.

*Petioles*.—Young Leaves: Subsessile. Mature Leaves: Size: From 1 to 1.5 mm long. Color: Near Greyed-Orange Group 165B.

*Hardiness*.—USDA Zone 5 (−20° F. to −10° F.).

*Vigor*.—Moderate, 1 to 2 m per year.

*Pests/diseases*.—No pest or disease problems noted.

Infloresence:

*Bloom period*.—March through May.

*Lastingness of individual bloom*.—2 weeks.

*Shape of inflorescence*.—Domed umbel.

*Flower arrangement*.—Spike in 3–5 whorls at the end of shoots.

*Number of flowers per umbel* (*typical and observed*.—Approximately 23–25.

*Umbel*.—Diameter: Approximately 100–120 mm (typical and observed). Length: Approximately 40–45 mm (typical and observed).

*Flower form*.—Tubular, two-lipped.

*Flower size*.—Length: 30 to 38 mm. Width at Base: Approximately 2 mm.

*Flower lips*.—Shape (Typial and Observed): Upper — oblong; lower — ligulate to falcate. Length (Typical and Observed): Upper — approximately 20–22 mm; Lower — approximately 30–32 mm. Width (Typical and Observed: Upper — approximately 12–15 mm; Lower — approximately 5 mm. Apex: Upper — tridentate/Sinuate; Lower — obtuse. Margin: Upper — entire; Lower — entire. Tube: Length approximately 22–25 mm; Width approximately 3 mm.

*Color*.—New Flowers: Near Yellow Group 4D. Older Flowers: Between Yellow Group 8A and 8B. New Lips: Upper and Lower — Near Yellow Group 4D. Old Lips: Upper and lower near Yellow Group 8A and 8C (the flower color turns from 8C to 8A as the flower ages. New Tube: Inner: Base near Yellow Green Group 149D; Top: Near Yellow Group 4D. Outer: Base near Yellow Green Group 149D; Top near Yellow Group 4D. Old Tube: Inner: Base near Yellow Green Group 150C; Top between Yellow Group 8B and 8C. Outer: Base near Yellow Green Group 150C; Top between Yellow Group 8B and 8C.

*Sepals*.—Length (Typical and Observed: Approximately 1.5 mm. Width (Typical and Observed: Approximately 1 mm. Apex: Acute. Margin: Entire. Color Upper and lower surfaces near Yellow Green Group 144A.

*Buds*.—Shape: Tubular, inflated, falcate. Size: Up to 35 mm long, 8 mm wide.

*Fragrance*.—Sweet, moderately strong.

*Peduncles*.—Length: Approximately 15 to 20 mm. Color: Yellow-Green Group near 144B.

Reproductive organs:

*Stamens*.—Number: 5. Length: 25 to 30 mm long. Color: Between Yellow Group 8A and 8B.

*Pistils*.—1.

*Stigma*.—1, Color Near Yellow Green Group 144B.

*Size*.—55 mm long.

*Anther color*.—Near Yellow-Orange Group 16B.

*Style color*.—Between Green-Yellow Group 1C and 1D.

*Ovary color*.—Between Yellow-Green Group 144B and 144D.

*Pollen*.—Amount: Numerous. Color Near Yellow Group 3D.

*Fruit*.—None observed.

I claim:

1. A new variety of *Lonicera periclymenum* plant substantially as shown and described.

* * * * *